United States Patent
Croll (10) Patent No.: US 10,500,054 B2
(45) Date of Patent: Dec. 10, 2019

(54) FEMORAL PROSTHESES WITH UPSIZING AND DOWNSIZING CAPABILITIES

(71) Applicant: Zimmer, Inc., Warsaw, IN (US)

(72) Inventor: Vanessa Croll, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 33 days.

(21) Appl. No.: 15/971,743

(22) Filed: May 4, 2018

(65) Prior Publication Data

US 2018/0325684 A1 Nov. 15, 2018

Related U.S. Application Data

(60) Provisional application No. 62/505,322, filed on May 12, 2017.

(51) Int. Cl.
*A61F 2/38* (2006.01)
*A61F 2/30* (2006.01)

(52) U.S. Cl.
CPC ............ *A61F 2/3859* (2013.01); *A61F 2/389* (2013.01); *A61F 2/3886* (2013.01); *A61F 2002/30616* (2013.01); *A61F 2002/3863* (2013.01)

(58) Field of Classification Search
CPC .......... A61F 2/28; A61F 2/3859; A61F 2/389; A61F 2/3886
See application file for complete search history.

(56) References Cited

U.S. PATENT DOCUMENTS

| 2008/0058947 A1 | 3/2008 | Earl et al. |
| 2013/0345820 A1 | 12/2013 | Maloney et al. |

FOREIGN PATENT DOCUMENTS

| FR | 2728782 | 7/1996 |
| WO | 2012173706 | 12/2012 |
| WO | 2018208612 | 11/2018 |

OTHER PUBLICATIONS

"International Application Serial No. PCT US2018 031177, International Search Report dated Jul. 31, 2018", 6 pgs.
"International Application Serial No. PCT US2018 031177, Written Opinion dated Jul. 31, 2018", 6 pgs.

*Primary Examiner* — Jason-Dennis N Stewart
(74) *Attorney, Agent, or Firm* — Schwegman Lundberg & Woessner, P.A.

(57) ABSTRACT

According to one example, a femoral prosthesis system is provided that has a plurality of sizing options using two families of femoral prostheses is disclosed. The second family of femoral prostheses can have a predetermined increase in femoral posterior condylar offset relative to the first family of femoral prosthesis. In one example, the second family of femoral prostheses can have the predetermined increase in the femoral posterior condylar offset while maintaining substantially a same femoral medial-lateral condylar extent relative to a comparably sized one of the first family of femoral prostheses.

22 Claims, 7 Drawing Sheets

FEMORAL PROSTHESES WITH UPSIZING AND DOWNSIZING CAPABILITIES

CLAIM OF PRIORITY

This application claims the benefit of U.S. Provisional Patent Application Ser. No. 62/505,322, filed on May 12, 2017, the benefit of priority of which is claimed hereby, and which is incorporated by reference herein in its entirety.

FIELD

The present subject matter relates to orthopedic prostheses and, more particularly, to prostheses and systems used in knee arthroplasties including revision knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral prosthesis implanted on the distal end of the femur, which articulates with a tibial bearing component and a tibial component implanted on the proximal end of a tibia to replicate the function of a healthy natural knee. Various types of arthroplasties are known including a total knee arthroplasty, where all of the articulating compartments of the joint are repaired with prosthetic components.

OVERVIEW

This disclosure pertains generally to femoral prostheses and systems for a knee arthroplasty including a revision knee arthroplasty. The present inventors have recognized, among other things, that it is desirable to offer versatile sizing options with regards to a combination of femoral posterior condylar offset and femoral medial-lateral condylar extent. More particularly, the present inventors have recognized a femoral prosthesis system that can have a plurality of sizing options using two families of femoral prostheses. The second family of femoral prostheses has a predetermined increase in the femoral posterior condylar offset relative to the first family of femoral prosthesis. In one example, the second family of femoral prostheses can have the predetermined increase in the femoral posterior condylar offset while maintaining substantially the same femoral medial-lateral condylar extent relative to the first family of femoral prostheses. Thus, for example, if sizing criteria dictate, a femoral prosthesis of a first size from the second family can be selected having a relatively larger femoral posterior condylar offset but a same femoral medial-lateral condylar extent to a correspondingly sized femoral prosthesis from the first family. Similarly, the systems allow for downsizing should sizing criteria dictate. For example, a femoral prosthesis of a first size from the first family can be selected having a femoral medial-lateral condylar extent that is larger than desired but having a femoral posterior condylar offset that is sized as desired. In such situation, the disclosed examples allow a correspondingly sized femoral prosthesis from the second family to be selected that has substantially a same femoral posterior condylar offset but a femoral medial-lateral condylar extent that differs from that of the femoral prosthesis of the first size from the first family by a predetermined amount. Such sizing versatility allows a patient appropriate femoral prosthesis from the first family or the second family to be selected more easily (e.g., selection is made using a consistent logical upsizing or downsizing scheme).

Regarding the first family of femoral prostheses, according to one example, the first family of femoral prostheses have a first range of posterior condylar offsets and a corresponding range of femoral medial-lateral condylar extents. The range for the femoral medial-lateral condylar extent of the first family can be between about 59 mm (for a size 1 femoral prosthesis) and about 80 mm (for a size 13 femoral prosthesis), for example. Similarly, the range of the posterior condylar offset can be between about 33 mm (for the size 1 femoral prosthesis) to about 52 mm (for the size 13 femoral prosthesis), for example. According to some examples, the femoral medial-lateral condylar extent can be substantially linearly incremented in a size increase from the size 1 to the size 13 femoral prosthesis such that for each increase in femoral size (e.g., going from a size 1 to size 3 or from a size 7 to a size 9) there is a corresponding known increase in the femoral medial-lateral condylar extent. The posterior condylar offset can be similarly substantially linearly incremented such that there is a known increase when moving up or down in prostheses size.

The present inventors have additionally recognized the prosthesis system can have the second family of femoral prostheses be compatible with the same tibial bearing component as a correspondingly sized femoral prosthesis from the first family of femoral prostheses. According to some examples, the second family of femoral prostheses can have a second range of posterior condylar offsets and corresponding femoral medial-lateral condylar extents. The range for the femoral medial-lateral condylar extent of the first family can be between about 59 mm (for a size 1+ femoral prosthesis) and about 77 mm (for a size 11+ femoral prosthesis), for example. Similarly, the range of the posterior condylar offset can be between about 37 mm (for the size 1+ femoral prosthesis) to about 52 mm (for the size 11+ femoral prosthesis), for example. According to some examples, the femoral medial-lateral condylar extent can be substantially linearly incremented in a size increase from the size 1+ to the size 11+ femoral prosthesis such that for each increase in femoral size there is a corresponding increase in the femoral medial-lateral condylar extent. The posterior condylar offset can be similarly substantially linearly incremented such that there is a known increase when moving up or down in prostheses size.

As discussed above, the size increase for the first family of femoral prostheses and the size increase for the second family of femoral prostheses can be related so as to be substantially the same (See FIGS. 5A-5C) according to some examples. However, the posterior condylar offset between the first family and the second family can be offset in that the femoral prostheses from the second family are always larger by a known amount (e.g., 3 mm) in the posterior condylar offset.

To further illustrate the apparatuses and systems disclosed herein, the following non-limiting examples are provided:

Example 1 is a system for knee arthroplasty that can optionally include: a first family having a first plurality of femoral prostheses with different stock sizes from one another, each of the first plurality of femoral prostheses having: a first stem housing extending along a first axis; and a first medial condyle and a first lateral condyle coupled to the first stem housing; wherein the first medial condyle and the first lateral condyle have a first posterior condylar offset as measured from the first axis to a first posterior-most point of the first medial condyle and the first lateral condyle; and wherein the first medial condyle and the first lateral condyle have a first femoral medial-lateral condylar extent from a medial most edge of the first medial condyle to a lateral most edge of the first lateral condyle; a second family having a second plurality of femoral prostheses with different stock sizes from one another, each of the second plurality of femoral prostheses having: a second stem housing extending along a second axis; and a second medial condyle and a second lateral condyle coupled to the second stem housing; wherein the second medial condyle and the second lateral condyle have a second posterior condylar offset from the second axis to a second posterior-most point of the second medial condyle and the second lateral condyle; and wherein the second medial condyle and the second lateral condyle have a second femoral medial-lateral condylar extent from a medial most edge of the second medial condyle to a lateral most edge of the second lateral condyle; wherein the first femoral medial-lateral condylar extent of at least one of the first plurality of femoral prostheses and the second femoral medial-lateral condylar extent of at least one of the second plurality of femoral prostheses are substantially the same.

In Example 2, the subject matter of Example 1 optionally can include the at least one of the first plurality of femoral prostheses and the at least one of the second plurality of femoral prostheses are configured to articulate with a same tibial bearing component.

In Example 3, the subject matter of any one or more of Examples 1-2 optionally can include the first posterior condylar offset of the at least one of the first plurality of femoral prostheses and the second posterior condylar offset of the at least one of the second plurality of femoral prostheses differ by a predetermined amount.

In Example 4, the subject matter of any one or more of Examples 1-3 optionally can include the predetermined amount comprises substantially 3 mm, and wherein the second medial condyle and a second lateral condyle are thickened along a posterior portion comprising at least a region between a posterior bone-contacting surface and a posterior portion of the J-curve when viewed in a sagittal plane relative to a corresponding thickness of the first medial condyle and the first lateral condyle.

In Example 5, the subject matter of any one or more of Examples 1-4 optionally can include the first posterior condylar offset of at least four of the first plurality of the femoral prostheses is substantially the same as the second posterior condylar offset of at least four of the second plurality of femoral prostheses.

In Example 6, the subject matter of any one or more of Examples 1-5 optionally include the first posterior condylar offset of at least six of the first plurality of the femoral prostheses is substantially the same as the second posterior condylar offset of at least six of the second plurality of femoral prostheses.

In Example 7, the subject matter of any one or more of Examples 1-6 optionally can include the first femoral medial-lateral condylar extent of at least four of the first plurality of the femoral prostheses is substantially the same as the second femoral medial-lateral condylar extent of at least four of the second plurality of femoral prostheses.

In Example 8, the subject matter of any one or more of Examples 1-7 optionally can include the first femoral medial-lateral condylar extent of at least six of the first plurality of the femoral prostheses is substantially the same as the second femoral medial-lateral condylar extent of at least six of the second plurality of femoral prostheses.

In Example 9, the subject matter of any one or more of Examples 1-8 optionally can include each of the different stock sizes of the first plurality of femoral prostheses differ with respect to the first femoral medial-lateral condylar extent by a first amount between a smaller size and a next larger size and each of the different stock sizes of the second plurality of femoral prostheses differ with respect to the second femoral medial-lateral condylar extent by a second amount between a corresponding smaller size and a corresponding next larger size, and wherein the first amount is substantially the same as the second amount.

In Example 10, the subject matter of any one or more of Examples 1-9 optionally can include each of the different stock sizes of the first plurality of femoral prostheses differ with respect to the first posterior condylar offset by a third amount between a smaller size and a next larger size and each of the different stock sizes of the second plurality of femoral prostheses differ with respect to the second posterior condylar offset by a fourth amount between a corresponding smaller size and a corresponding next larger size, and wherein the third amount is substantially the same as the fourth amount.

Example 11 is a system for knee arthroplasty can optionally include: a first family having a first plurality of femoral prostheses with different stock sizes from one another, each of the first plurality of femoral prostheses having: a first stem housing extending along a first axis; and a first medial condyle and a first lateral condyle coupled to the first stem housing; wherein the first medial condyle and the first lateral condyle have a first posterior condylar offset as measured from the first axis to a first posterior-most point of the first medial condyle and the first lateral condyle; and wherein the first medial condyle and the first lateral condyle have a first femoral medial-lateral condylar extent as measured from a medial most edge of the first medial condyle to a lateral most edge of the first lateral condyle; a second family having a second plurality of femoral prostheses with different stock sizes from one another, each of the second plurality of femoral prostheses having: a second stem housing extending along a second axis; and a second medial condyle and a second lateral condyle coupled to the second stem housing; wherein the second medial condyle and the second lateral condyle have a second posterior condylar offset as measured from the second axis to a second posterior-most point of the second medial condyle and the second lateral condyle; and wherein the second medial condyle and the second lateral condyle have a second femoral medial-lateral condylar extent as measured from a medial most edge of the second medial condyle to a lateral most edge of the second lateral condyle; wherein the first posterior condylar offset of at least one of the first plurality of femoral prostheses and the second posterior condylar offset of at least one of the second plurality of femoral prostheses are substantially the same; and wherein the first femoral medial-lateral condylar extent of the at least one of the first plurality of femoral prostheses and the second femoral medial-lateral condylar extent of the at least one of the second plurality of femoral prostheses differ by a first predetermined amount.

In Example 12, the subject matter of Example 11 optionally can include at least one of the first medial condyle and the first lateral condyle have a first thickness at a posterior portion between a first posterior bone-contacting surface and the first posterior-most point and at least one of the second medial condyle and the second lateral condyle have a second thickness at a corresponding posterior portion between a second posterior bone-contacting surface and the second posterior-most point, and wherein the first thickness differs from the second thickness by a second predetermined amount.

In Example 13, the subject matter of Example 12 optionally can include a third thickness of the at least one of the first medial condyle and the first lateral condyle as measured between a first posterior chamfer and an articular surface differs by a third predetermined amount from a fourth thickness of at least one of the second medial condyle and the second lateral condyle as measured between a corresponding second posterior chamfer and a corresponding articular surface.

In Example 14, the subject matter of Example 13 optionally can include an anterior bone-contacting surface of the at least one of the second plurality of femoral prostheses is disposed relatively nearer the second axis by a fourth predetermined amount than a corresponding anterior bone-contacting surface of the at least one of the first plurality of femoral prostheses.

In Example 15, the subject matter of Example 14 optionally can include one or both of the first predetermined amount and the second predetermined amount comprises substantially 3 mm, the third predetermined amount comprises substantially 1 mm and the fourth predetermined amount comprises substantially 1 mm.

In Example 16, the subject matter of any one or more of Examples 11-15 optionally can include the at least one of the first plurality of femoral prostheses and the at least one of the second plurality of femoral prostheses are configured to articulate with a same tibial bearing component.

In Example 17, the subject matter of any one or more of Examples 11-16 optionally can include the first posterior condylar offset of at least four of the first plurality of the femoral prostheses is substantially the same as the second posterior condylar offset of at least four of the second plurality of femoral prostheses.

In Example 18, the subject matter of any one or more of Examples 11-17 optionally can include the first posterior condylar offset of at least six of the first plurality of the femoral prostheses is substantially the same as the second posterior condylar offset of at least six of the second plurality of femoral prostheses.

In Example 19, the subject matter of any one or more of Examples 11-18 optionally can include the first femoral medial-lateral condylar extent of at least four of the first plurality of the femoral prostheses is substantially the same as the second femoral medial-lateral condylar extent of at least four of the second plurality of femoral prostheses.

In Example 20, the subject matter of any one or more of Examples 11-19 optionally can include the first femoral medial-lateral condylar extent of at least six of the first plurality of the femoral prostheses is substantially the same as the second femoral medial-lateral condylar extent of at least six of the second plurality of femoral prostheses.

In Example 21, the subject matter of any one or more of Examples 11-20 optionally can include each of the different stock sizes of the first plurality of femoral prostheses differ with respect to the first femoral medial-lateral condylar extent by a first amount between a smaller size and a next larger size and each of the different stock sizes of the second plurality of femoral prostheses differ with respect to the second femoral medial-lateral condylar extent by a second amount between a corresponding smaller size and a corresponding next larger size, and wherein the first amount is substantially the same as the second amount.

In Example 22, the subject matter of any one or more of Examples 11-21 optionally can include each of the different stock sizes of the first plurality of femoral prostheses differ with respect to the first posterior condylar offset by a third amount between a smaller size and a next larger size and each of the different stock sizes of the second plurality of femoral prostheses differ with respect to the second posterior condylar offset by a fourth amount between a corresponding smaller size and a corresponding next larger size, and wherein the third amount is substantially the same as the fourth amount.

In Example 23, the systems of any one or any combination of Examples 1-22 can optionally be configured such that all elements or options recited are available to use or select from.

These and other examples and features of the present devices and systems will be set forth in part in the following Detailed Description. This overview is intended to provide a summary of subject matter of the present patent application. It is not intended to provide an exclusive or exhaustive removal of the invention. The detailed description is included to provide further information about the present patent application.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates femoral prostheses and systems. The systems, for example, can include a first family having a first plurality of femoral prostheses with different stock sizes from one another. The system can additional include a second family having a second plurality of femoral prostheses with different stock sizes from one another. Each of the first plurality of femoral prostheses can have a first stem housing extending along a first axis and a first medial condyle and a first lateral condyle coupled to the first stem housing. The first medial condyle and the first lateral condyle can have a first posterior condylar offset as measured from the first axis to a first posterior-most point of the first medial condyle and the first lateral condyle. The first medial condyle and the first lateral condyle can have a first femoral medial-lateral condylar extent as measured from a medial most edge of the first medial condyle to a lateral most edge of the first lateral condyle. Similarly, the second stem housing can extending along a second axis and a second medial condyle and a second lateral condyle can be coupled to the second stem housing. The second medial condyle and the second lateral condyle can have a second posterior condylar offset as measured from the second axis to a second posterior-most point of the second medial condyle and the second lateral condyle. The second medial condyle and the second lateral condyle can have a second femoral medial-lateral condylar extent as measured from a medial most edge of the second medial condyle to a lateral most edge of the second lateral condyle. The first femoral medial-lateral condylar extent of at least one of the first plurality of femoral prostheses and the second femoral medial-lateral condylar extent of at least one of the second plurality of femoral prostheses can be substantially the same according to some examples.

The present application relates to prostheses and systems that can be used in a knee arthroplasty and/or as part of a later knee revision surgery. As described herein, the term system or assembly can include both tibial prosthesis and a femoral prosthesis. This application focuses on aspects of the femoral prosthesis, which can include the stem housing, the medial condyle and the lateral condyle. As discussed previously, the femoral prostheses can be part of the system used to simplify sizing and offer various femoral options that can be compatible with the same tibial bearing component. Additional features and benefits of the various examples provided herein will be discussed and/or will be apparent to one of ordinary skill in the art.

As used herein, the terms "proximal" and "distal" should be given their generally understood anatomical interpretation. The term "proximal" refers to a direction generally toward the torso of a patient, and "distal" refers to the opposite direction of proximal, i.e., away from the torso of a patient. It should be understood that the use of the terms "proximal" and "distal" should be interpreted as though the patient were standing with the knee joint in extension despite the apparatuses described herein generally being used with the knee joint in flexion. The intent is to differentiate the terms "proximal" and "distal" from the terms "anterior" and "posterior". As used herein, the terms "anterior" and "posterior" should be given their generally understood anatomical interpretation. Thus, "posterior" refers to a rear of the patient, e.g., a back of the knee. Similarly, "anterior" refers to a front of the patient, e.g., a front of the knee. Thus, "posterior" refers to the opposite direction of "anterior". Similarly, the term "lateral" refers to the opposite direction of "medial".

Figure 1:
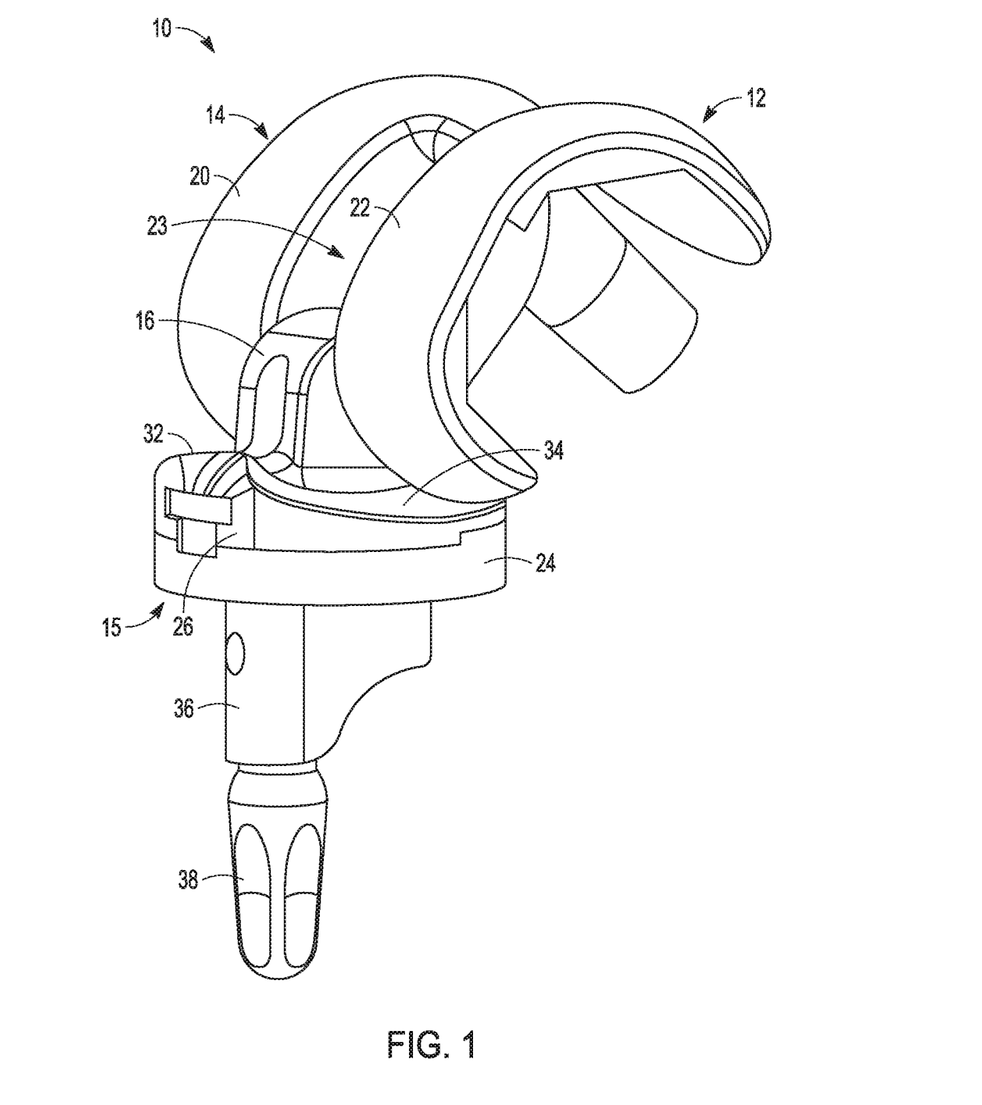
FIG. 1 shows a perspective view of a prosthesis assembly including a femoral prosthesis, a tibial bearing component and a tibial baseplate according to an example of the present application.
Figure 2:
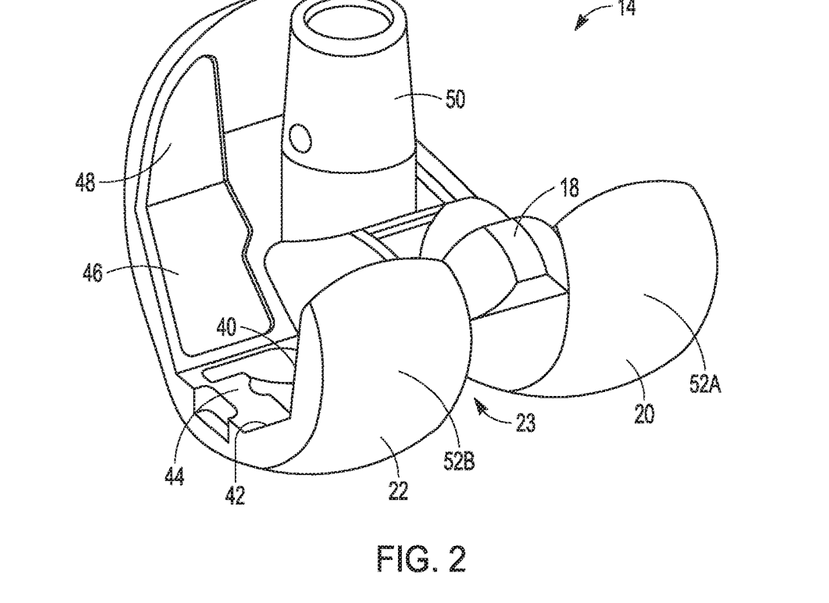
FIG. 2 shows a perspective view of the femoral prosthesis of FIG. 1 according to an example of the present application.
Figure 2A:
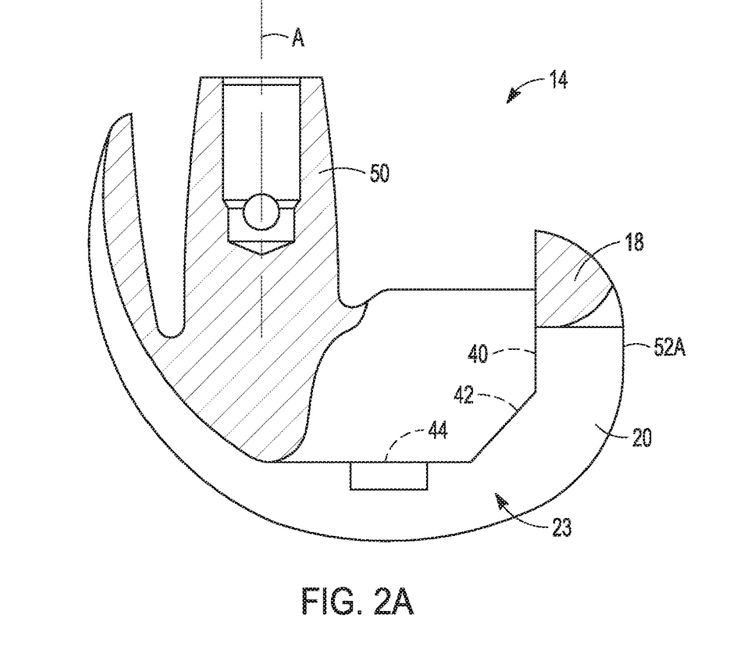
FIG. 2A shows a cross-sectional view of FIG. 2 in a sagittal plane extending through an intercondylar space between a medial condyle and a lateral condyle according to an example of the present application.
Figure 3:
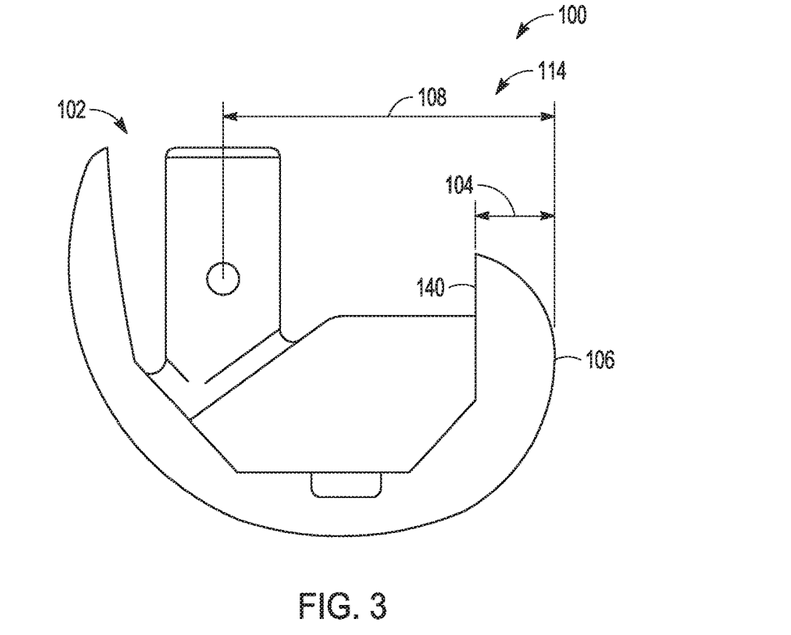
FIGS. 3 and 3A show a system that includes a first femoral prosthesis of a first size from a first family and a second femoral prosthesis from a second family, the second femoral prosthesis of a corresponding size but having an additional thickness in a posterior portion as compared with the first femoral prosthesis according to an example of the present application.
Figure 3A:
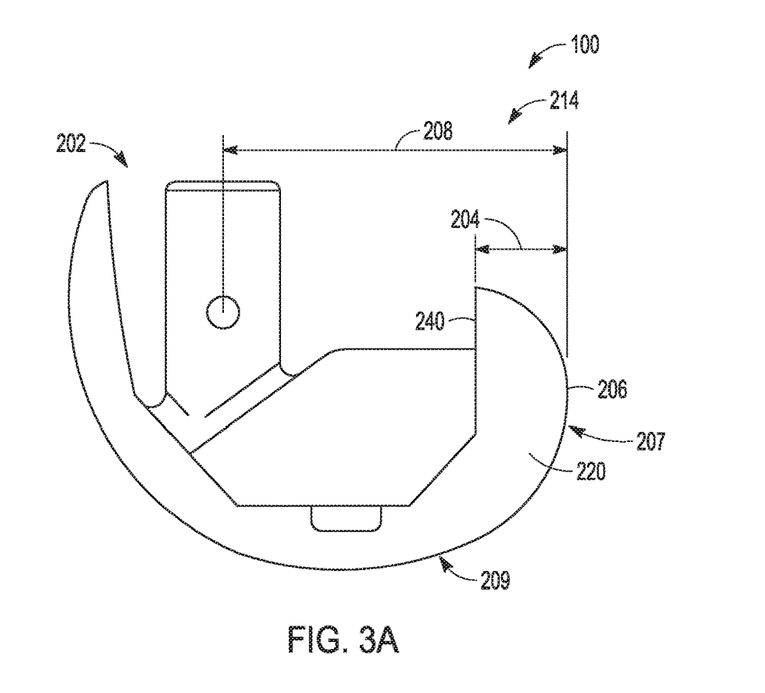

FIG. 1 illustrates a prosthesis assembly 10 that can be used as part of a system 12 described herein. The assembly 10 and system 12 can include a femoral prosthesis 14 and a tibial prosthesis 15. In the example of FIG. 1, the prosthesis assembly 10 is shown in a perspective view with the femoral prosthesis 14 articulated relative to the tibial prosthesis 15 to 135° of flexion. FIGS. 2A, 3 and 3A show various examples of the femoral prosthesis 14 (sometimes indicated with other reference numbers) in a cross-sectional view along a sagittal plane. The sagittal plane extends along the anterior-posterior direction and the proximal-distal direction of the femoral prosthesis illustrated.

According to the examples provided herein, the prosthesis assembly 10 and system 12 can utilize posterior stabilized (PS) prostheses. Thus, the tibial prosthesis 15 can include a spine 16 and the femoral prosthesis 14 can include a cam 18 (FIGS. 2 and 2A). The spine 16 and the cam 18 can designed to cooperate with one another to stabilize the femoral prosthesis 14 with respect to tibial prosthesis 15 in lieu of a posterior cruciate ligament (PCL). However, other prosthesis designs are contemplated including a mid-level constraint (MLC) design, a cruciate retaining (CR) design, a constrained condylar (CC), an ultra-congruent (UC) design, for example. CR tibial prostheses are generally used in surgical procedures which retain the PCL. The CR and UC designs omit the spine 16 and cam 18. In any case, the femoral prosthesis 14 defines an intercondylar space 23 between medial and lateral condyles 20 and 22 (shown in FIGS. 1 and 2). In the case of a CR or UC, this intercondylar space can entirely open and uninterrupted by the cam 18 as it is in FIGS. 1, 2 and 2A.

Turning to the components illustrated in FIG. 1, the tibial prosthesis 15 can include a tibial bearing component 26 and a tibial baseplate 24. The tibial bearing component 26 can include the spine 16 (FIGS. 2 and 2A), a proximal medial articular surface 32 and a proximal lateral articular surface 34. The tibial baseplate 24 can include a keel 36. Additional components such as a stem 38 can be used with the prosthesis assembly 10 in some examples.

As shown in FIG. 1, the femoral prosthesis 14 can be disposed atop and can articulate relative to the tibial prosthesis 15. Such articulation can be between the medial and lateral femoral condyles 20 and 22 and the proximal medial articular surface 32 and the proximal lateral articular surface 34, respectively. The proximal medial articular surface 32 and the proximal lateral articular surface 34 can be shaped (e.g., curved) to facilitate such articulation during knee joint flexion. The spine 16 (FIGS. 2 and 2A) of the tibial bearing component 26 can be centrally located between the proximal medial articular surface 32 and the proximal lateral articular surface 34. The spine 16 can be configured to engage with the cam 18 during flexion. Such engagement provides additional stability that would otherwise be offered by ligaments such as the PCL.

The tibial bearing component 26 can be secured to the tibial baseplate 24 as shown in FIG. 1. Such securement can be facilitated by the use of rails, notches, bosses, an insert, and/or fastener according to various examples.

FIGS. 2 and 2A show the femoral prosthesis 14. FIG. 2 shows the femoral prosthesis 14 from a posterior-medial position. FIG. 2A shows the femoral prosthesis 14 in a cross-section along the sagittal plane, the cross-section extending along the intercondylar space 23 and bisecting the cam 18.

FIGS. 2 and 2A show the cam 18, which can have multiple radii according to the illustrated example. In addition to the medial and lateral condyles 20 and 22 (only the medial condyle 20 is shown in FIG. 2A), the femoral prosthesis 14 can include a posterior bone-interfacing surface 40 (shown partially dashed in FIG. 2A), a posterior bone-interfacing chamfer surface 42 (shown dashed in FIG. 2A), a distal bone-interfacing surface 44 (shown dashed in FIG. 2A), an anterior bone-interfacing chamfer surface 46 (not shown in FIG. 2A), an anterior bone-interfacing surface 48 (not shown in FIG. 2A) and a stem housing 50. The medial and lateral condyles 20 and 22 can include medial and lateral articular surfaces 52A and 52B, respectively. When viewed in the sagittal plane, (as in FIG. 2A) the articular surfaces 52A and 52B can form J-curves (only one is shown in FIG. 2A).

The cam 18 can be positioned at a posterior end of the intercondylar space 23 and can extend between the medial and lateral condyles 20 and 22. As shown in FIG. 2, portions of the posterior bone-interfacing surface 40, the posterior bone-interfacing chamfer surface 42, the distal bone-interfacing surface 44, the anterior bone-interfacing chamfer surface 46 and the anterior bone-interfacing surface 48 can be formed by the medial and lateral condyles 20 and 22. The medial and lateral articular surfaces 52A and 52B can be disposed opposite (spaced by a thickness of the medial and lateral condyles 20 and 22) from the posterior bone-interfacing surface 40, the posterior bone-interfacing chamfer surface 42, the distal bone-interfacing surface 44, the anterior bone-interfacing chamfer surface 46 and the anterior bone-interfacing surface 48. The medial and lateral condyles 20 and 22 can have varying thicknesses both medial-lateral and anterior-posterior.

The posterior bone-interfacing surface 40, the posterior bone-interfacing chamfer surface 42, the distal bone-interfacing surface 44, the anterior bone-interfacing chamfer surface 46 and the anterior bone-interfacing surface 48 are configured to abut resected portions of the femur (not shown) upon implantation of the femoral prosthesis 14. The stem housing 50 can be positioned generally between the medial and lateral condyles 20 and 22 and can be coupled thereto. The stem housing 50 can be positioned anterior of the intercondylar space 23. The stem housing 50 can extend generally proximally and can be symmetrical about a first axis A as shown in FIG. 2A. In some examples, the stem housing 50 can be canted medial-lateral so as to be both extend medial-lateral and proximal in extent from interconnection between the medial and lateral condyles 20 and 22.

FIGS. 3 and 3A shows examples of femoral prostheses 114, 214 that can be used according to a system 100. The femoral prostheses 114, 214 can be configured in a manner similar to that of the example femoral prosthesis 14 previously described. The femoral prosthesis 114 can be from a first family 102 of femoral prostheses of which the femoral prosthesis 114 is exemplary of one distinct predetermined size. Similarly, the femoral prosthesis 214 can be from a second family 202 of femoral prostheses of which the femoral prosthesis 214 is exemplary of one distinct predetermined size. The femoral prosthesis 114 can be similar in size with respect to the femoral prosthesis 214 according to some examples. Such similarity can be that a medial-lateral condylar extent (shown subsequently) of the femoral prosthesis 114 can be substantially the same as the medial-lateral condylar extent of the femoral prosthesis 214. Thus, according to some examples, the femoral prostheses 114, 214 can be compatible to articulate with the same tibial prosthesis (i.e. the same bearing component) as is discussed further subsequently. The medial-lateral condylar extent is illustrated in reference to FIGS. 4-5C and can comprise a distance from a medial most edge of the medial condyle to a lateral most edge of the lateral condyle.

However, as shown in FIGS. 3 and 3A, the femoral prosthesis 114 can differ in size from the femoral prosthesis 214 in that the femoral prosthesis 214 has a different thickness 204 between at least the posterior bone-interfacing surface 240 and the articular surface 206 than the femoral prosthesis 114. Thus, a thickness 104 between the posterior bone-interfacing surface 140 and the articular surface 106 differs from the thickness 204 as shown in the example of FIGS. 3 and 3A. Thus, for the femoral prosthesis 214, the second medial condyle 220 and the second lateral condyle (only the medial condyle 220 is shown in FIGS. 3 and 3A) are thickened along a posterior portion 207 comprising at least a region between the posterior bone-contacting surface 240 and a posterior portion of the J-curve 209 when viewed in a sagittal plane relative to a corresponding thickness of the first medial condyle and the first lateral condyle of the femoral prosthesis 114.

Due to the difference between the thickness 104 and the thickness 204, the femoral prosthesis 114 can have a posterior condylar offset 108 that differs from a posterior condylar offset 208 of the femoral prosthesis 214. According to some examples, the posterior condylar offset 108 can differ from the posterior condylar offset 208 by a predetermined amount (e.g., 1, 2, 3, 4 or 5 mm). Indeed, in the illustrated embodiment of FIGS. 3 and 3A, the predetermined amount can comprise substantially 3 mm difference between the posterior condylar offset 208 and the posterior condylar offset 108.

Figure 4:
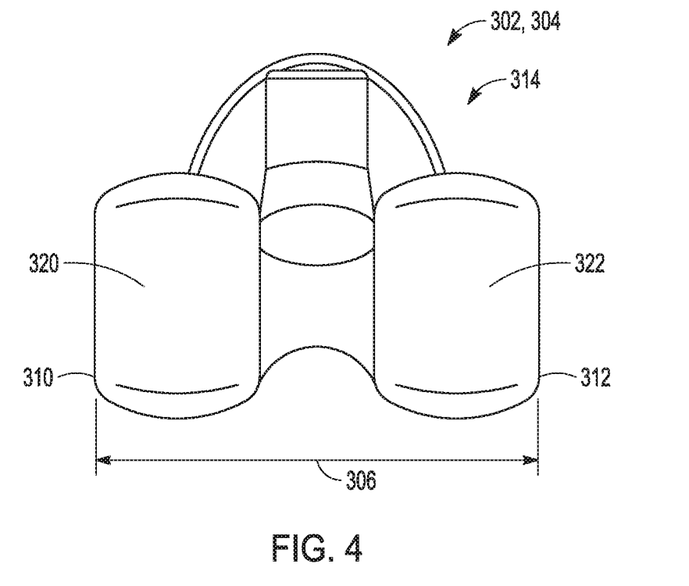
FIGS. 4 and 4A show a femoral prosthesis of either the first family or the second family showing femoral medial-lateral condylar extent and a posterior condylar offset according to an example of the present application.
Figure 4A:
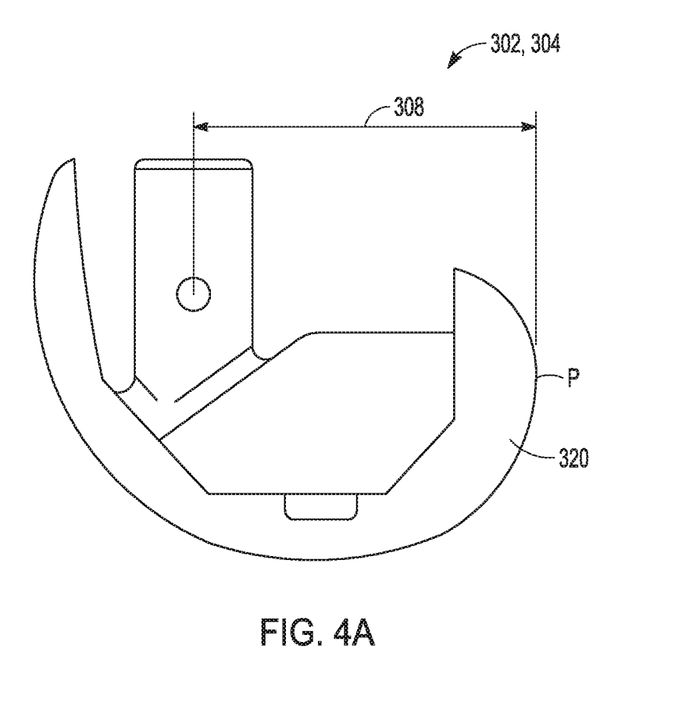

FIGS. 4 and 4A shows a femoral prosthesis 314 that can comprise one of either the first family of femoral prostheses 302 or the second family of femoral prostheses 304 discussed subsequently in regards to FIGS. 5A to 5C. As shown in FIGS. 4 and 4A, the femoral prosthesis 314 can include a medial-lateral condylar extent 306 and a posterior condylar offset 308.

The medial-lateral condylar extent 306 can be from a medial most edge 310 of a medial condyle 320 to a lateral most edge 312 of a lateral condyle 322. The posterior condylar offset 308 can extend from an axis A of a stem housing 314 to a posterior-most point P of at least one of the medial condyle 320 and the lateral condyle 322.

Figure 5A:
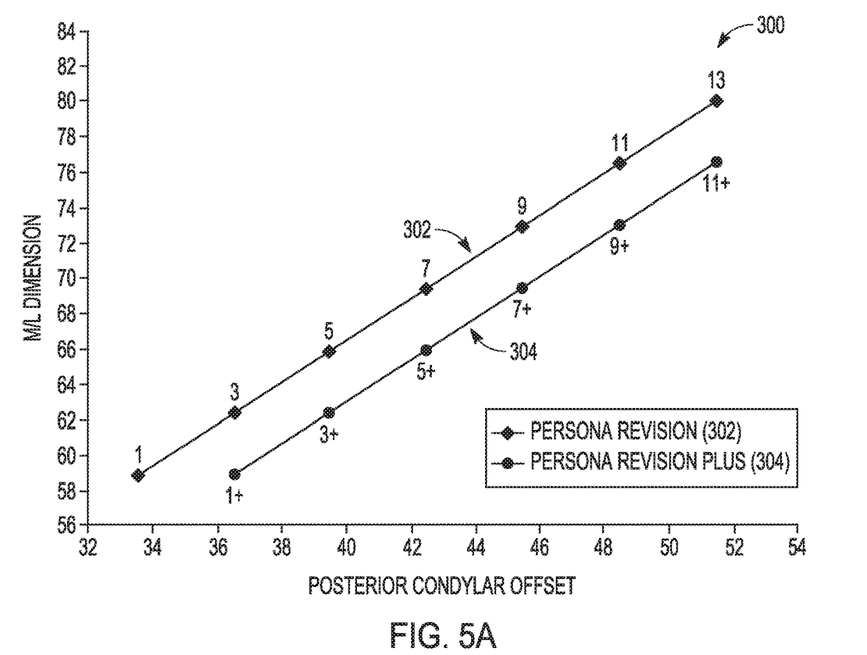
FIG. 5A is a graph of a system of femoral prostheses from the first family and the second family, the graph plotting the difference in sizes of the first family and the second family as measured by the femoral medial-lateral condylar extent and the posterior condylar offset according to an example of the present application.
Figure 5B:
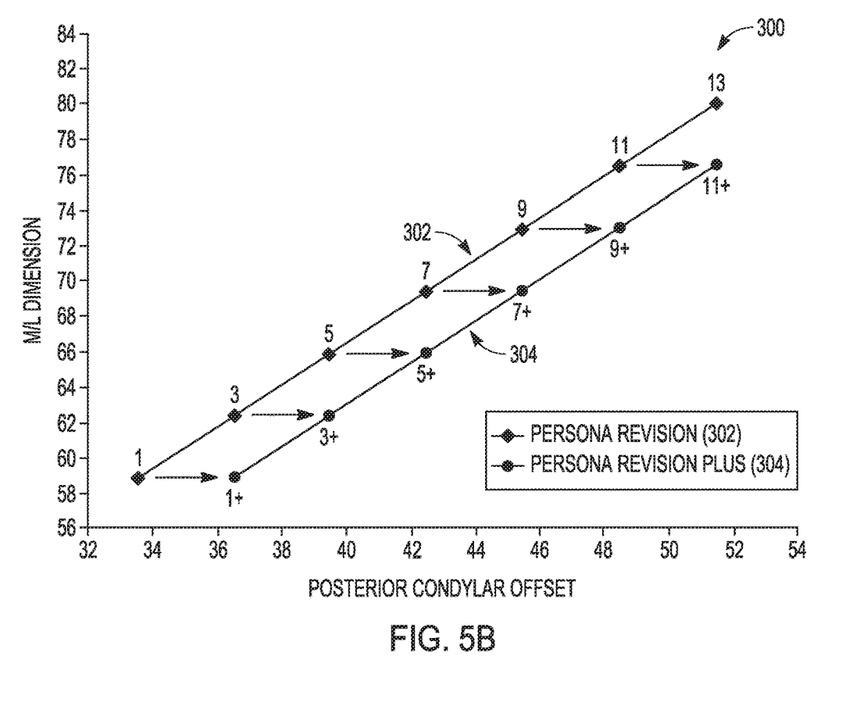
FIG. 5B is the graph of FIG. 5A but shows an upsizing technique whereby a physician can increase the posterior condylar offset while maintaining the femoral medial-lateral condylar extent by swapping a femoral prosthesis of a first size from the first family for a femoral prosthesis of the second family according to an example of the present application.
Figure 5C:
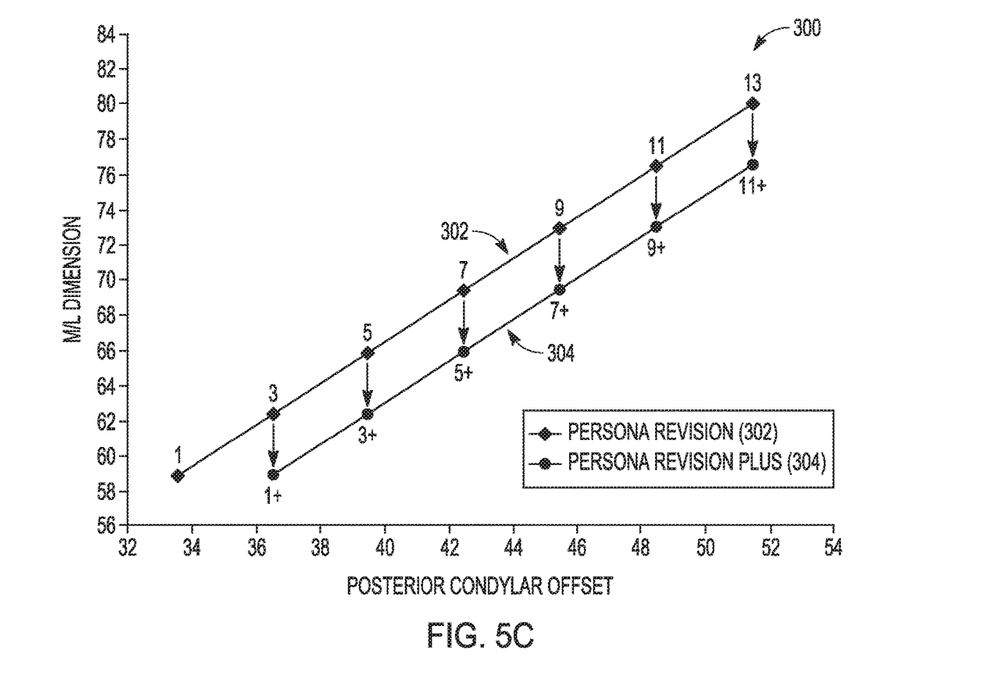
FIG. 5C is the graph of FIG. 5A but shows a downsizing technique whereby the physician can reduce the femoral medial-lateral condylar extent but maintain the posterior condylar offset by swapping a femoral prosthesis of a first size from the first family for a femoral prosthesis of the second family according to an example of the present application.

FIGS. 5A-5C provide a system 300 comprised of the first family of femoral prostheses 302 and the second family of femoral prostheses 304. Each of the first family of femoral prostheses 302 and the second family of femoral prostheses 304 include a plurality of distinct sizes as shown in the plot of FIGS. 5A-5C. In the example of FIGS. 5A-5C, the first family of femoral prostheses 302 can have seven distinct sizes indicated as sizes 1, 3, 5, 7, 9, 11 and 13. The second family of femoral prostheses 304 can have six distinct sizes indicated as sizes 1+, 3+, 5+, 7+, 9+ and 11+.

According to the example of FIG. 5A, the posterior condylar offset of at least four of the first family of femoral prostheses 302 (the first family of femoral prostheses 302 being of different distinct sizes from one another) can be substantially the same as the posterior condylar offset of at least four of the second family of femoral prostheses 304 (the second family of femoral prosthesis 304 being of different distinct sizes from one another). According to some examples, the posterior condylar offset of at least six of the first family of femoral prostheses 302 can be substantially the same as the posterior condylar offset of at least six of the second family of femoral prostheses 304 (e.g., sizes 3 and 1+ can have substantially the same posterior condylar offset, sizes 5 and 3+ can have substantially the same posterior condylar offset, sizes 7 and 5+ can have substantially the same posterior condylar offset, sizes 9 and 7+ can have substantially the same posterior condylar offset, sizes 11 and 9+ can have substantially the same posterior condylar offset and sizes 13 and 11+ can share substantially the same posterior condylar offset).

Similarly, the femoral medial-lateral condylar extent of at least four of the first family of femoral prostheses 302 (the first family of femoral prostheses 302 being of different distinct sizes from one another) can substantially the same as the femoral medial-lateral condylar extent of at least four of the second family of femoral prostheses 304 (the second family of femoral prosthesis 304 being of different distinct sizes from one another). According to some examples, the femoral medial-lateral condylar extent of at least six of the first family of femoral prostheses 302 can be substantially the same as the femoral medial-lateral condylar extent of at least six of the second family of femoral prostheses 304 (e.g., sizes 1 and 1+ can have substantially the same femoral medial-lateral condylar extent, sizes 3 and 3+ can have substantially femoral medial-lateral condylar extent, sizes 5 and 5+ can have substantially the same femoral medial-lateral condylar extent, sizes 7 and 7+ can have substantially the same femoral medial-lateral condylar extent, sizes 9 and 9+ can have substantially the same femoral medial-lateral condylar extent and sizes 11 and 11+ can share substantially the same femoral medial-lateral condylar extent).

As shown in FIGS. 5A and 5B, each of the different stock sizes of the first family of plurality of femoral prostheses 302 can differ with respect to the femoral medial-lateral condylar extent by a first amount (e.g., a few mm such as 3 mm) between a smaller size and a next larger size and each of the different stock sizes. Similarly, the second family of femoral prostheses 304 can differ with respect to the femoral medial-lateral condylar extent by a second amount (e.g., a few mm such as 3 mm) between a corresponding smaller size and a corresponding next larger size. In some cases, the first amount can be substantially the same as the second amount.

FIG. 5B shows that the system 300 can have the first family of femoral prostheses 302 be compatible with the second family of femoral prostheses 304 for a flexion fill. In particular, up to six of the first family of femoral prostheses 302 can be compatible with corresponding sizes of the second family of femoral prostheses 304 such that the posterior condylar offset can be changed by swapping a particular size of prosthesis from the first family of femoral prostheses 302 for a corresponding size of the second family of femoral prostheses 304 (e.g., a size 1 can be swapped for a size 1+, etc.). According to the example of FIG. 5B, the posterior condylar offset can be changed by a predetermined amount (e.g., 3 mm) when swapping a particular size of prosthesis from the first family of femoral prostheses 302 for a corresponding size of the second family of femoral prostheses 304. Furthermore, according to the example of FIG. 5B, while the posterior condylar offset can be changed, the femoral medial-lateral condylar extent between the first size of the first family of femoral prostheses 302 and the correspondingly size of the second family of femoral prostheses 304 can remain substantially the same.

FIG. 5C shows the system 300 can be used for a downsizing in the femoral medial-lateral condylar extent while the flexion fill can be maintained. In particular, up to six of the first family of femoral prostheses 302 can be compatible with other sizes of the second family of femoral prostheses 304 such that the femoral medial-lateral condylar extent can be changed by swapping a particular size of prosthesis from the first family of femoral prostheses 302 for a second size of the second family of femoral prostheses 304 (e.g., a size 3 can be swapped for a size 1+, etc.). According to the example of FIG. 5C, while the femoral medial-lateral condylar extent can be changed, the posterior condylar offset between the first size of the first family of femoral prostheses 302 and the second size of the second family of femoral prostheses 304 can remain substantially the same.

Figure 6:
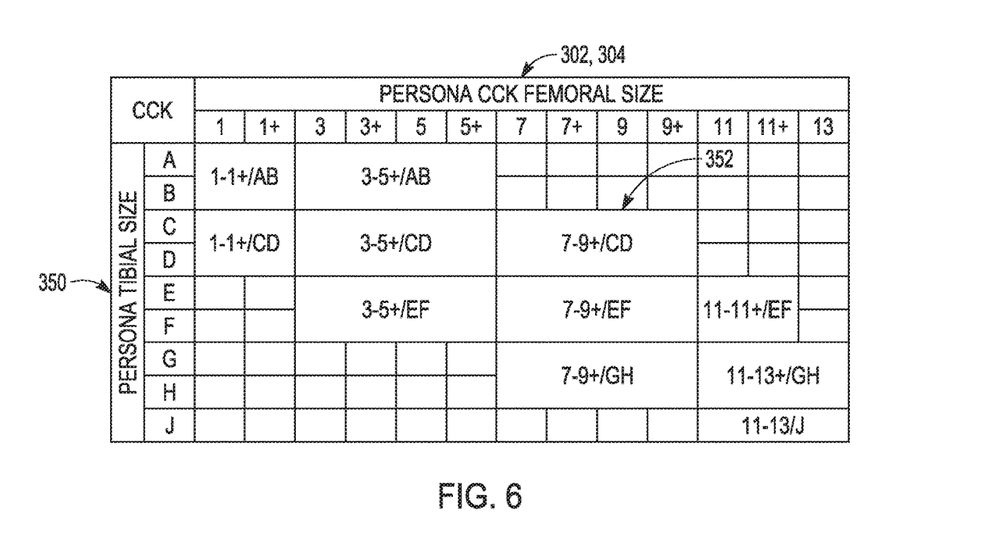
FIG. 6 shows a sizing chart for a family of tibial bearing components relative to a family of femoral prostheses and tibial baseplates and in accordance with an example of the present application

FIG. 6 shows a sizing chart for the family of tibial baseplates 350 relative to the first and second families of femoral prostheses 302, 304. As shown in FIG. 6 the least one of the first family of femoral prostheses 302 and the least one of the second family of femoral prostheses 304 can be configured to articulate with a same tibial bearing component. More particularly, the sizing chart shows the first and second families of femoral prostheses 302, 304 can have at least thirteen different stock sizes 1 to 13 (including + sizes). As previously discussed and illustrated, each femoral prosthesis of the first and second families can be of a same design class but can include distinct sizes having different femoral medial-lateral condylar extent and/or posterior condylar offset.

The family of tibial baseplates 350 can have at least nine different stock sizes A to J. As shown in FIG. 6, a family of tibial bearing components 352 can be configured such that eleven stock sizes exist and that combinations of the at least nine different stock sizes of the family of tibial baseplates are compatible for operable use (e.g. to facilitate a desired articulation similar to that of a natural knee) with the at least thirteen different stock sizes of the first and second families of femoral prostheses 302, 304.

FIG. 6 also illustrates that at least six of the different stock sizes of tibial bearing components 352 are configured to be are compatible with at least four of the thirteen stock sizes of femoral prostheses while also being compatible with at least two of the tibial components 350.

According to further examples, eleven of the at least thirteen different stock sizes of the first and second families of femoral prostheses 302, 304 can be compatible for operable use with nine of the at least eleven different stock sizes of the family of tibial bearing components 352. According to further examples, twelve of the at least thirteen different stock sizes of the first and second families of femoral prostheses 302, 304 can be compatible for operable use with at least two of the at least eleven different stock sizes of the tibial bearing baseplates 350.

This overlapping sizing and the provision of many different compatible sizes can have benefits including providing for increased stability of the medial condyle of the femoral prosthesis. Additionally, the overlapping sizing allows for the flexion fill and downsizing in the femoral medial-lateral condylar extent as discussed previously with respect to FIGS. 5A-5C.

Figure 7:
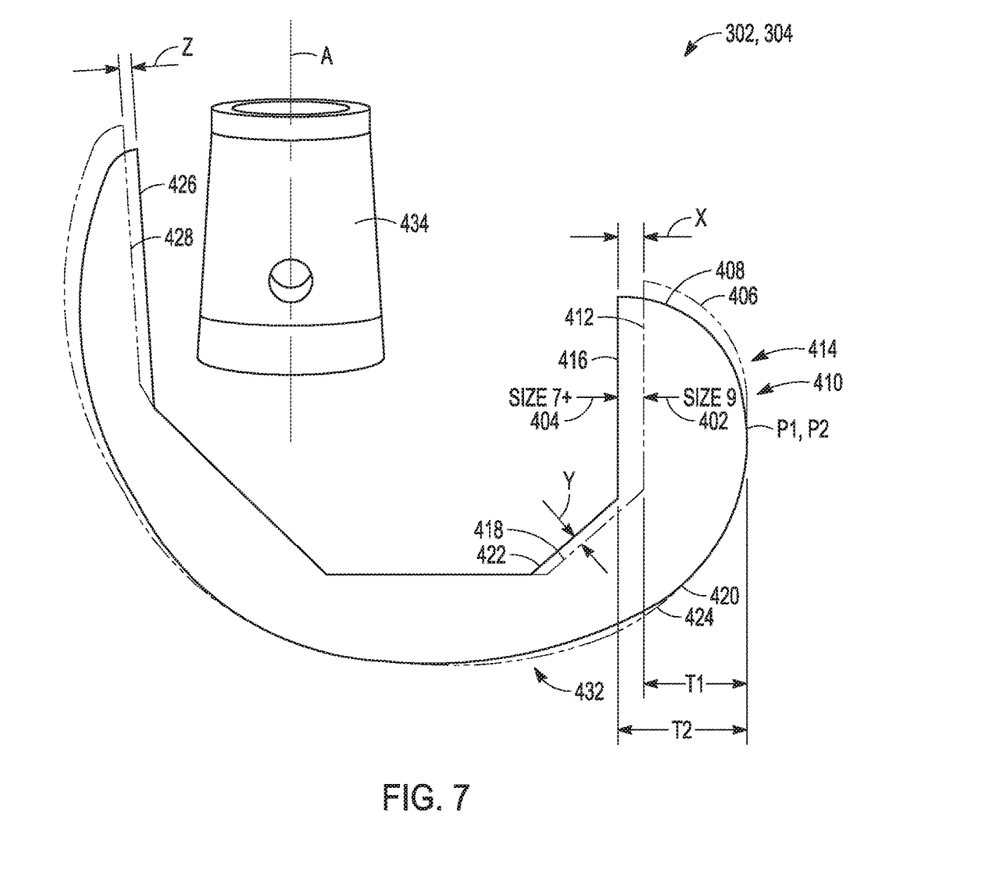
FIG. 7 shows example of the downsizing of FIG. 5C with regard to two juxtapositioned prostheses having substantially a same posterior condylar offset including one femoral prosthesis of the first family and one femoral prosthesis of the second family according to an example of the present application.

FIG. 7 provides a specific example of the downsizing in the femoral medial-lateral condylar extent while the flexion fill (substantially the same posterior condylar offset) can be maintained as previously discussed in reference to FIG. 5C. FIG. 7 shows a geometry of a first prosthesis 402 of a first size (e.g., size 9) of the first family of femoral prostheses 302 in a sagittal plane superimposed on the geometry of a second prosthesis 404 of a second size (e.g., size 7+) of the second family of femoral prostheses 304 in a sagittal plane.

FIG. 7 shows the first prosthesis 402 can include one of a first medial condyle or first lateral condyle (collectively 406). Similarly, the second prosthesis 404 can include one of a second medial condyle or second lateral condyle (collectively 408).

As shown in FIG. 7, at least one of the first medial condyle and the first lateral condyle 406 can have a first thickness T1 at a posterior portion 410 between a first posterior bone-contacting surface 412 and the first posterior-most point P1. Similarly, at least one of the second medial condyle and the second lateral condyle 408 can have a second thickness T2 at a corresponding posterior portion 414 between a second posterior bone-contacting surface 416 and the second posterior-most point P2 (points P1 and P2 can be disposed at a same posterior location). As shown in FIG. 7, according to some examples the first thickness T1 can differ from the second thickness T2 by a predetermined amount (e.g., X as shown in FIG. 7).

According to the example of FIG. 7, a third thickness of at least one of the first medial condyle and the first lateral condyle 406 as measured between a first posterior chamfer 418 and an articular surface 420 of the first prosthesis 402 differs by a predetermined amount Y from a fourth thickness of at least one of the second medial condyle and the second lateral condyle 408 as measured between a corresponding second posterior chamfer 422 and a corresponding articular surface 424 of the second prosthesis 404.

In some examples, an anterior bone-contacting surface 426 of the second prosthesis 404 (one of the second plurality of femoral prostheses 304 previously discussed) can be disposed relatively nearer to a stem housing axis A by another predetermined amount Z than a corresponding anterior bone-contacting surface 428 of the first prosthesis 402 (one of the first plurality of femoral prostheses 302).

As previously discussed, the downsizing in the femoral medial-lateral condylar extent can be by a predetermined amount (e.g., a few mm). Similarly, the predetermined amount X can be substantially 3 mm (or another desired amount), the predetermined amount Y can comprise substantially 1 mm (or another desired amount) and the predetermined amount Z comprises substantially 1 mm (or another desired amount).

At least one of the first medial condyle and the first lateral condyle 406 and at least one of the second medial condyle and the second lateral condyle 408 can have a similar sagittal J-curve 430 along a posterior and distal portion thereof 432 from the first and second posterior-most points P1 and P2, respectively, to a point distal of the stem housing 434, respectively.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A system for knee arthroplasty comprising:
   a first family having a first plurality of femoral prostheses with different stock sizes from one another, each of the first plurality of femoral prostheses having:
      a first stem housing extending along a first axis; and
      a first medial condyle and a first lateral condyle coupled to the first stem housing;
      wherein the first medial condyle and the first lateral condyle have a first posterior condylar offset as measured from the first axis to a first posterior-most point of the first medial condyle and the first lateral condyle; and
      wherein the first medial condyle and the first lateral condyle have a first femoral medial-lateral condylar extent from a medial most edge of the first medial condyle to a lateral most edge of the first lateral condyle;

a second family having a second plurality of femoral prostheses with different stock sizes from one another, each of the second plurality of femoral prostheses having:
   a second stem housing extending along a second axis; and
   a second medial condyle and a second lateral condyle coupled to the second stem housing;
   wherein the second medial condyle and the second lateral condyle have a second posterior condylar offset from the second axis to a second posterior-most point of the second medial condyle and the second lateral condyle; and
   wherein the second medial condyle and the second lateral condyle have a second femoral medial-lateral condylar extent from a medial most edge of the second medial condyle to a lateral most edge of the second lateral condyle;
wherein the first femoral medial-lateral condylar extent of at least one of the first plurality of femoral prostheses and the second femoral medial-lateral condylar extent of at least one of the second plurality of femoral prostheses are substantially the same.

2. The system of claim 1, wherein the at least one of the first plurality of femoral prostheses and the at least one of the second plurality of femoral prostheses are configured to articulate with a same tibial bearing component.

3. The system of claim 1, wherein the first posterior condylar offset of the at least one of the first plurality of femoral prostheses and the second posterior condylar offset of the at least one of the second plurality of femoral prostheses differ by a predetermined amount.

4. The system of claim 1, wherein the predetermined amount comprises substantially 3 mm, and wherein the second medial condyle and a second lateral condyle are thickened along a posterior portion comprising at least a region between a posterior bone-contacting surface and a posterior portion of the J-curve when viewed in a sagittal plane relative to a corresponding thickness of the first medial condyle and the first lateral condyle.

5. The system of claim 1, wherein the first posterior condylar offset of at least four of the first plurality of the femoral prostheses is substantially the same as the second posterior condylar offset of at least four of the second plurality of femoral prostheses.

6. The system of claim 1, wherein the first posterior condylar offset of at least six of the first plurality of the femoral prostheses is substantially the same as the second posterior condylar offset of at least six of the second plurality of femoral prostheses.

7. The system of claim 1, wherein the first femoral medial-lateral condylar extent of at least four of the first plurality of the femoral prostheses is substantially the same as the second femoral medial-lateral condylar extent of at least four of the second plurality of femoral prostheses.

8. The system of claim 1, wherein the first femoral medial-lateral condylar extent of at least six of the first plurality of the femoral prostheses is substantially the same as the second femoral medial-lateral condylar extent of at least six of the second plurality of femoral prostheses.

9. The system of claim 1, wherein each of the different stock sizes of the first plurality of femoral prostheses differ with respect to the first femoral medial-lateral condylar extent by a first amount between a smaller size and a next larger size and each of the different stock sizes of the second plurality of femoral prostheses differ with respect to the second femoral medial-lateral condylar extent by a second amount between a corresponding smaller size and a corresponding next larger size, and wherein the first amount is substantially the same as the second amount.

10. The system of claim 1, wherein each of the different stock sizes of the first plurality of femoral prostheses differ with respect to the first posterior condylar offset by a third amount between a smaller size and a next larger size and each of the different stock sizes of the second plurality of femoral prostheses differ with respect to the second posterior condylar offset by a fourth amount between a corresponding smaller size and a corresponding next larger size, and wherein the third amount is substantially the same as the fourth amount.

11. A system for knee arthroplasty comprising:
   a first family having a first plurality of femoral prostheses with different stock sizes from one another, each of the first plurality of femoral prostheses having:
      a first stem housing extending along a first axis; and
      a first medial condyle and a first lateral condyle coupled to the first stem housing;
      wherein the first medial condyle and the first lateral condyle have a first posterior condylar offset as measured from the first axis to a first posterior-most point of the first medial condyle and the first lateral condyle; and
      wherein the first medial condyle and the first lateral condyle have a first femoral medial-lateral condylar extent as measured from a medial most edge of the first medial condyle to a lateral most edge of the first lateral condyle;
   a second family having a second plurality of femoral prostheses with different stock sizes from one another, each of the second plurality of femoral prostheses having:
      a second stem housing extending along a second axis; and
      a second medial condyle and a second lateral condyle coupled to the second stem housing;
      wherein the second medial condyle and the second lateral condyle have a second posterior condylar offset as measured from the second axis to a second posterior-most point of the second medial condyle and the second lateral condyle; and
      wherein the second medial condyle and the second lateral condyle have a second femoral medial-lateral condylar extent as measured from a medial most edge of the second medial condyle to a lateral most edge of the second lateral condyle;
   wherein the first posterior condylar offset of at least one of the first plurality of femoral prostheses and the second posterior condylar offset of at least one of the second plurality of femoral prostheses are substantially the same; and
   wherein the first femoral medial-lateral condylar extent of the at least one of the first plurality of prostheses and the second femoral medial-lateral condylar extent of the at least one of the second plurality of femoral prostheses differ by a first predetermined amount.

12. The system of claim 11, wherein at least one of the first medial condyle and the first lateral condyle have a first thickness at a posterior portion between a first posterior bone-contacting surface and the first posterior-most point and at least one of the second medial condyle and the second lateral condyle have a second thickness at a corresponding posterior portion between a second posterior bone-contacting surface and the second posterior-most point, and wherein the first thickness differs from the second thickness by a second predetermined amount.

13. The system of claim 12, wherein a third thickness of the at least one of the first medial condyle and the first lateral condyle as measured between a first posterior chamfer and an articular surface differs by a third predetermined amount from a fourth thickness of at least one of the second medial condyle and the second lateral condyle as measured between a corresponding second posterior chamfer and a corresponding articular surface.

14. The system of claim 13, wherein an anterior bone-contacting surface of the at least one of the second plurality of femoral prostheses is disposed relatively nearer the second axis by a fourth predetermined amount than a corresponding anterior bone-contacting surface of the at least one of the first plurality of femoral prostheses.

15. The system of claim 14, wherein one or both of the first predetermined amount and the second predetermined amount comprises substantially 3 mm, the third predetermined amount comprises substantially 1 mm and the fourth predetermined amount comprises substantially 1 mm.

16. The system of claim 11, wherein the at least one of the first plurality of femoral prostheses and the at least one of the second plurality of femoral prostheses are configured to articulate with a same tibial bearing component.

17. The system of claim 11, wherein the first posterior condylar offset of at least four of the first plurality of the femoral prostheses is substantially the same as the second posterior condylar offset of at least four of the second plurality of femoral prostheses.

18. The system of claim 11, wherein the first posterior condylar offset of at least six of the first plurality of the femoral prostheses is substantially the same as the second posterior condylar offset of at least six of the second plurality of femoral prostheses.

19. The system of claim 11, wherein the first femoral medial-lateral condylar extent of at least four of the first plurality of the femoral prostheses is substantially the same as the second femoral medial-lateral condylar extent of at least four of the second plurality of femoral prostheses.

20. The system of claim 11, wherein the first femoral medial-lateral condylar extent of at least six of the first plurality of the femoral prostheses is substantially the same as the second femoral medial-lateral condylar extent of at least six of the second plurality of femoral prostheses.

21. The system of claim 11, wherein each of the different stock sizes of the first plurality of femoral prostheses differ with respect to the first femoral medial-lateral condylar extent by a first amount between a smaller size and a next larger size and each of the different stock sizes of the second plurality of femoral prostheses differ with respect to the second femoral medial-lateral condylar extent by a second amount between a corresponding smaller size and a corresponding next larger size, and wherein the first amount is substantially the same as the second amount.

22. The system of claim 11, wherein each of the different stock sizes of the first plurality of femoral prostheses differ with respect to the first posterior condylar offset by a third amount between a smaller size and a next larger size and each of the different stock sizes of the second plurality of femoral prostheses differ with respect to the second posterior condylar offset by a fourth amount between a corresponding smaller size and a corresponding next larger size, and wherein the third amount is substantially the same as the fourth amount.

* * * * *